United States Patent [19]

Bouchard et al.

[11] Patent Number: 5,580,998
[45] Date of Patent: Dec. 3, 1996

[54] PROCESS FOR PREPARING TAXOIDS

[75] Inventors: Hervé Bouchard, Ivry Sur Seine; Jean-Dominique Bourzat, Vincennes; Alain Commercon, Vitry-Sur-Seine, all of France

[73] Assignee: Rhone-Poulenc Rorer S.A., Antony, France

[21] Appl. No.: 479,199

[22] Filed: Jun. 7, 1995

Related U.S. Application Data

[62] Division of Ser. No. 162,984, Dec. 8, 1993.

[30] Foreign Application Priority Data

Dec. 9, 1992 [FR] France .................. 92 14813

[51] Int. Cl.$^6$ .................. C07D 305/14
[52] U.S. Cl. .................. 549/510; 549/511
[58] Field of Search .................. 549/510, 511

[56] References Cited

U.S. PATENT DOCUMENTS 4,814,470  3/1989  Colin et al. .................. 514/449
5,254,580  10/1993  Chen et al. .................. 514/499

FOREIGN PATENT DOCUMENTS

WO94/13655  6/1994  WIPO.
WO94/13654  6/1994  WIPO.

OTHER PUBLICATIONS

Guéritte–Voegelein et al., "Relationships between the Structure of Taxol Analogues and Their Antimitotic Activity," J. Med. Chem. 1991, 34, 992–998.

Klein et al., "Synthesis of Ring B–Rearranged Taxane Analogs," J. Org. Chem. 1994, 59, 2370–2373.

*Primary Examiner*—Ba K. Trinh
*Attorney, Agent, or Firm*—Finnegan, Henderson, Farabow, Garrett & Dunner, L.L.P.

[57] ABSTRACT

The invention relates to a process for preparing taxoids of formula I herein that includes comprising the steps of esterifying a baccatin III derivative of the formula VI herein, treating the compound obtained in acidic medium, and optionally removing a protecting group to give the desired taxoid product.

28 Claims, No Drawings

PROCESS FOR PREPARING TAXOIDS

This is a division of application Ser. No. 08/162,984, filed Dec. 8, 1993 pending.

The present invention relates to new taxoids of general formula:

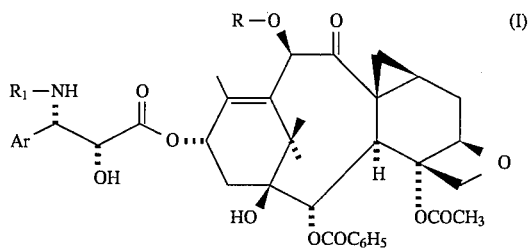

their preparation and pharmaceutical compositions containing them.

In general formula (I),

Ar represents an aryl radical,

R represents a hydrogen atom or an acetyl, alkoxyacetyl or alkyl radical, $R_1$ represents a benzoyl radical or a radical $R_2$—O—CO— in which $R_2$ represents:

a straight or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 11 carbon atoms, these radicals being optionally substituted by one or more substituents chosen from halogen atoms and hydroxy radicals, alkyloxy radicals containing 1 to 4 carbon atoms, dialkylamino radicals in which each alkyl portion contains 1 to 4 carbon atoms, piperidino radicals, morpholino radicals, 1-piperazinyl radicals (optionally substituted at position 4 by an alkyl radical containing 1 to 4 carbon atoms or by a phenylalkyl radical whose alkyl portion contains 1 to 4 carbon atoms), cycloalkyl radicals containing 3 to 6 carbon atoms, cycloalkenyl radicals containing 4 to 6 carbon atoms, phenyl radicals, cyano radicals, carboxy radicals or alkyloxycarbonyl radicals whose alkyl portion contains 1 to 4 carbon atoms, or a phenyl radical optionally substituted by one or more atoms or radicals chosen from halogen atoms and alkyl radicals containing 1 to 4 carbon atoms or alkyloxy radicals containing 1 to 4 carbon atoms, or a saturated or unsaturated 4- to 6-membered nitrogen-containing heterocyclyl radical optionally substituted by one or more alkyl radicals containing 1 to 4 carbon atoms, it being understood that the cycloalkyl, cycloalkenyl or bicycloalkyl radicals may be optionally substituted by one or more alkyl radicals containing 1 to 4 carbon atoms.

Preferably, Ar represents a phenyl or α- or β-naphthyl radical optionally substituted by one or more atoms or radicals chosen from halogen atoms (fluorine, chlorine, bromine, or iodine) and alkyl, alkenyl, alkynyl, aryl, aryalkyl, alkoxy, alkylthio, aryloxy, arylthio, hydroxy, hydroxyalkyl, mercapto, formyl, acyl, acylamino, aroylamino, alkoxycarbonylamino, amino, alkylamino, dialkylamino, carboxy, alkoxycarbonyl, carbamoyl, dialkylcarbamoyl, cyano, nitro and trifluoromethyl radicals, it being understood that the alkyl radicals and the alkyl portions of the other radicals contain 1 to 4 carbon atoms, that the alkenyl and alkynyl radicals contain 2 to 8 carbon atoms and that the aryl radicals are phenyl or α- or β-naphthyl radicals or alternatively Ar represents a 5-membered aromatic heterocyclic radical containing one or more atoms, which are identical or different, chosen from nitrogen, oxygen or sulphur atoms, optionally substituted by one or more substituents, which are identical or different, chosen from halogen atoms (fluorine, chlorine, bromine or iodine) and alkyl radicals containing 1 to 4 carbon atoms, aryl radicals containing 6 to 10 carbon atoms, alkoxy radicals containing 1 to 4 carbon atoms, aryloxy radicals containing 6 to 10 carbon atoms, amino radicals, alkylamino radicals containing 1 to 4 carbon atoms, dialkylamino radicals in which each alkyl portion contains 1 to 4 carbon atoms, acylamino radicals in which the acyl portion contains 1 to 4 carbon atoms, alkoxycarbonylamino radicals containing 1 to 4 carbon atoms, acyl radicals containing 1 to 4 carbon atoms, arylcarbonyl radicals in which the aryl portion contains 6 to 10 carbon atoms, cyano radicals, carboxy radicals, carbamoyl radicals, alkylcarbamoyl radicals in which the alkyl portion contains 1 to 4 carbon atoms, dialkylcarbamoyl radicals in which each alkyl portion contains 1 to 4 carbon atoms or alkoxycarbonyl radicals in which the alkoxy portion contains 1 to 4 carbon atoms.

More particularly, Ar represents a phenyl, 2- or 3-thienyl or 2- or 3-furyl radical optionally substituted by one or more atoms or radicals, which are identical or different, chosen from halogen atoms and alkyl, alkoxy, amino, alkylamino, dialkylamino, acylamino, alkoxycarbonylamino and trifluoromethyl radicals.

Still more particularly, Ar represents a phenyl radical optionally substituted by a chlorine or fluorine atom or by an alkyl (methyl), alkoxy (methoxy), dialkylamino (diethylamino), acylamino (acetylamino) or alkoxycarbonylamino (tert-butoxycarbonylamino) or 2- or 3-thienyl or 2- or 3-furyl radical.

Of even more special interest are the products of general formula (I) in which Ar represents a phenyl radical and $R_1$ represents a benzoyl or tert-butoxycarbonyl radical.

According to the present invention, the new taxoids of general formula (I) can be obtained from a product of general formula:

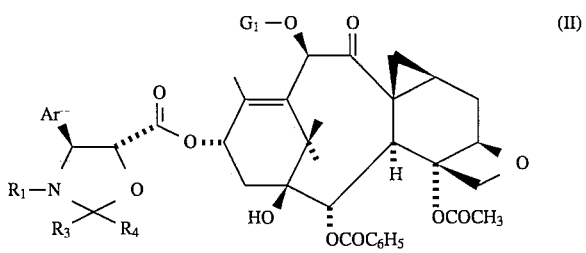

in which Ar and $R_1$ are defined as above and $R_3$ and $R_4$, which are identical or different represent a hydrogen atom or an alkyl radical containing 1 to 4 carbon atoms, or an aralkyl radical whose alkyl portion contains 1 to 4 carbon atoms and the aryl portion preferably represents a phenyl radical optionally substituted by one or more alkoxy radicals containing 1 to 4 carbon atoms, or an aryl radical preferably representing a phenyl radical optionally substituted by one or more alkoxy radicals containing 1 to 4 carbon atoms, or alternatively $R_3$ represents an alkoxy radical containing 1 to 4 carbon atoms or a trihalomethyl radical such as trichloromethyl or a phenyl radical substituted by a trihalomethyl radical such as trichloromethyl and $R_4$ represents a hydrogen atom, or alternatively $R_3$ and $R_4$ form, together with the carbon atom to which they are attached, a 4- to 7-membered ring, and $G_1$ represents a hydrogen atom or an acetyl, alkoxyacetyl or alkyl radical or a hydroxy-protecting group, the procedure being carried out, according to the meanings of $R_3$ and $R_4$, in the following manner:

1) when $R_3$ represents a hydrogen atom or an alkoxy radical containing 1 to 4 carbon atoms or an optionally substituted aryl radical and $R_4$ represents a hydrogen atom, the product of general formula (II) is treated in acidic medium in order to obtain a product of general formula:

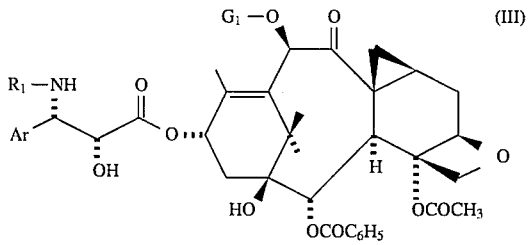

(III)

in which Ar, $R_1$ and $G_1$ are defined as above, whose $G_1$ radical is, if necessary, replaced by a hydrogen atom.

The deprotection of the side chain of the product of general formula (II) can also be carried out in the presence of an inorganic acid (hydrochloric acid or sulphuric acid) or an organic acid (acetic acid, methanesulphonic acid, trifluoromethanesulphonic acid or p-toluenesulphonic acid), used alone or in the form of a mixture, the procedure being carried out in an organic solvent chosen from alcohols (methanol, ethanol or isopropanol), ethers (tetrahydrofuran, diisopropyl ether or methyl t-butyl ether), esters (ethyl acetate, isopropyl acetate or n-butyl acetate), aliphatic hydrocarbons (pentane, hexane or heptane), halogenated aliphatic hydrocarbons (dichloromethane or 1,2-dichloroethane), aromatic hydrocarbons (benzene, toluene or xylenes) and nitriles (acetonitrile) at a temperature of between −10° and 60° C., preferably between 15° and 30° C. The acid may be used in a catalytic or stoichiometric quantity or in excess.

The deprotection can also be carried out under oxidizing conditions, using for example ammonium cerium(IV) nitrate in an acetonitrile-water mixture or 2,3-dichloro-5,6-dicyano-1,4-benzoquinone in water.

The deprotection can also be carried out under reducing conditions, for example by hydrogenolysis in the presence of a catalyst.

When $G_1$ represents a protecting group, it is preferably a 2,2,2-trichloroethoxycarbonyl or 2-(2-trichloromethylpropoxy) carbonyl radical whose replacement by a hydrogen atom is carried out using zinc, optionally combined with copper, in the presence of acetic acid, at a temperature of between 20° and 60° C. or by means of an inorganic or organic acid such as hydrochloric acid or acetic acid in a solution in an aliphatic alcohol containing 1 to 3 carbon atoms or in an aliphatic ester such as ethyl acetate, isopropyl acetate or n-butyl acetate in the presence of zinc optionally combined with copper, or alternatively, when $G_1$ represents an alkoxycarbonyl radical, its optional replacement by a hydrogen atom is carried out by treatment in alkaline medium or by the action of a zinc halide under conditions which do not affect the rest of the molecule. Generally, the alkaline treatment is carried out by the action of ammonia in aqueous-alcoholic medium, at a temperature close to 20° C. Generally, the treatment with a zinc halide, preferably zinc iodide is carried out in methanol at a temperature close to 20° C.

2) when $R_3$ and $R_4$, which are identical or different, represent an alkyl radical containing 1 to 4 carbon atoms, or an aralkyl radical whose alkyl portion contains 1 to 4 carbon atoms and the aryl portion is preferably an optionally substituted phenyl radical, or alternatively $R_3$ represents a trihalomethyl radical or a phenyl radical substituted by a trihalomethyl radical and $R_4$ represents a hydrogen atom, or alternatively $R_3$ and $R_4$ form, together with the carbon atom to which they are attached, a 4- to 7-membered ring, the product of general formula (II) is converted to the product of general formula:

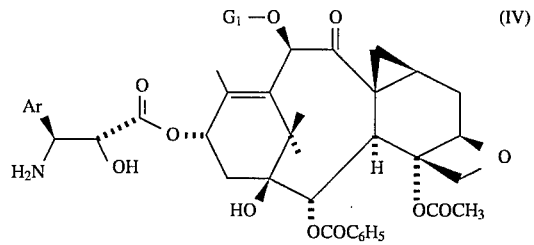

(IV)

in which Ar and $G_1$ are defined as above, which is acylated by means of benzoyl chloride or a reactive derivative of general formula:

$$R_2\text{—O—CO—X} \quad (V)$$

in which $R_2$ is defined as above and X represents a halogen atom (fluorine or chlorine) or a residue —O—$R_2$ or —O—CO—O—$R_2$, to give a product of general formula (III) in which Ar, $R_1$ and $G_1$ are defined as above, whose $G_1$ radical is, if necessary, replaced by a hydrogen atom.

The products of general formula (IV) can be obtained by treating a product of general formula (II), in which Ar, $R_1$ and $G_1$ are defined as above, $R_3$ and $R_4$, which are identical or different, represent an alkyl, aralkyl or aryl radical, or alternatively $R_3$ and $R_4$ form together with the carbon atom to which they are attached a 4- to 7-membered ring, with an inorganic acid (hydrochloric acid or sulphuric acid) or an organic acid (formic acid) optionally in an alcohol containing 1 to 3 carbon atoms (methanol, ethanol or isopropanol) at a temperature of between 0° and 50° C. Preferably, formic acid is used at a temperature close to 20° C.

The acylation of the product of general formula (IV) by means of benzoyl chloride or a reactive derivative of general formula (V) is carried out in an inert organic solvent chosen from esters such as ethyl acetate, isopropyl acetate or n-butyl acetate and halogenated aliphatic hydrocarbons such as dichloromethane or 1,2-dichloroethane in the presence of an inorganic base such as sodium bicarbonate or an organic base such as triethylamine. The reaction is carried out at a temperature of between 0° and 50° C., preferably close to 20° C.

When the radical $G_1$ represents a protecting group, its replacement by a hydrogen atom is carried out under the conditions described above.

The products of general formula (II) can be obtained according to one of the following methods: 1) by esterification of the product of general formula:

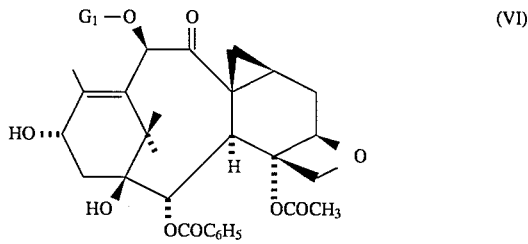

(VI)

in which $G_1$ is defined as above, by means of an acid of general formula:

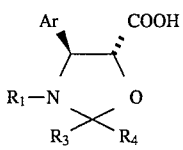 (VII)

in which Ar, $R_1$, $R_3$ and $R_4$ are defined as above, or of a derivative of this acid.

The esterification by means of an acid of general formula (VII) can be carried out in the presence of a condensing agent (carbodiimide, reactive carbonate) and an activating agent (aminopyridine) in an organic solvent (ether, ester, ketones, nitriles, aliphatic hydrocarbons, halogenated aliphatic hydrocarbons or aromatic hydrocarbons) at a temperature of between −10° and 90° C.

The esterification may also be performed using the acid of general formula (VII) in anhydride form, the procedure being carried out in the presence of an activating agent (aminopyridine) in an organic solvent (ethers, esters, ketones, nitriles, aliphatic hydrocarbons, halogenated aliphatic hydrocarbons or aromatic hydrocarbons) at a temperature of between 0° and 90° C.

The esterification can also be performed using the acid of general formula (VII) in halide form or in anhydride form with an aliphatic or aromatic acid, optionally prepared in situ, in the presence of a base (tertiary aliphatic amine), the procedure being carried out in an organic solvent (ethers, esters, ketones, nitriles, aliphatic hydrocarbons, halogenated aliphatic hydrocarbons or aromatic hydrocarbons) at a temperature of between 0° and 80° C.

The acid of general formula (VII) can be obtained by saponification of an ester of general formula:

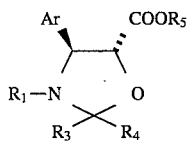 (VIII)

in which Ar, $R_1$, $R_3$ and $R_4$ are defined as above and $R_5$ represents an alkyl radical containing 1 to 4 carbon atoms optionally substituted by a phenyl radical.

Generally, the saponification is carried out by means of an inorganic base (alkali metal hydroxide, carbonate or bicarbonate) in aqueous-alcoholic medium (methanol-water) at a temperature of between 10° and 40° C.

The ester of general formula (VIII) can be obtained by the action of a product of general formula:

 (IX)

in which $R_3$ and $R_4$ are defined as above in the form of a dialkylacetal or an enol alkyl ether, on an ester of general formula:

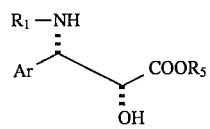 (X)

in which Ar, $R_1$ and $R_3$ are defined as above, the procedure being carried out in an inert organic solvent (aromatic hydrocarbon) in the presence of a strong inorganic acid (sulphuric acid) or organic acid (p-toluenesulphonic acid optionally in the form of a pyridinium salt) at a temperature of between 0° C. and the boiling temperature of the reaction mixture.

The ester of general formula (X) can be obtained by the action of a product of general formula (V) on an ester of general formula:

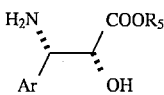 (XI)

in which Ar and $R_5$ are defined as above, the procedure being carried out in an organic solvent (ester, halogenated aliphatic hydrocarbon) in the presence of an inorganic or organic base at a temperature of between 0° and 50° C.

The product of general formula (XI) can be obtained by reduction of an azide of general formula:

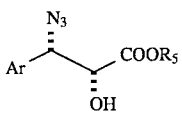 (XII)

in which Ar and $R_5$ are defined as above, by means of hydrogen in the presence of a catalyst such as palladium on carbon, the procedure being carried out in an organic solvent (ester).

The product of general formula (XII) can be obtained by the action of an azide such as trimethylsilyl azide in the presence of zinc chloride or an alkali metal (sodium, potassium or lithium) azide in aqueous-organic medium (water-tetrahydrofuran) at a temperature of between 20° C. and the boiling temperature of the reaction mixture, on an epoxide of general formula:

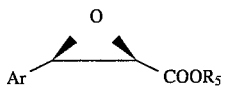 (XIII)

in which Ar and $R_5$ are defined as above, optionally prepared in situ.

The epoxide of general formula (XIII) can be obtained, optionally in situ, by dehydrohalogenation of a product of general formula:

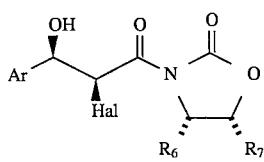 (XIV)

in which Ar is defined as above, Hal represents a halogen atom, preferably a bromine atom, and $R_6$ and $R_7$, which are identical or different, represent a hydrogen atom or an alkyl radical containing 1 to 4 carbon atoms or a phenyl radical, at least one being an alkyl radical or a phenyl radical, by means of an alkali-metal alcoholate, optionally prepared in situ, in an inert organic solvent such as tetrahydrofuran at a temperature of between −80° C. and 25° C.

The product of general formula (XIV) can be obtained by the action of an aldehyde of general formula:

 Ar—CHO (XV)

in which Ar is defined as above, on a halide of general

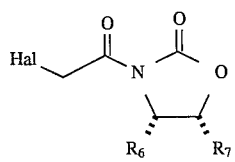 (XVI)

in which Hal, $R_6$ and $R_7$ are defined as above, anionized beforehand.

Generally, the procedure is carried out in an inert organic solvent chosen from ethers (ethyl ether) and halogenated aliphatic hydrocarbons (methylene chloride) at a temperature of between −80° and 25° C., in the presence of a tertiary amine (triethylamine) and an enolysing agent (di-n-butylboron triflate).

The product of general formula (XVI) can be obtained by the action of a halide of a haloacetic acid, preferably bromoacetic acid bromide, on the corresponding oxazolidinone.

The product of general formula (XI) can be obtained by hydrogenolysis of a product of general formula:

$$\text{Ph} \overset{CH_3}{\underset{\vdots}{\curlywedge}} NH \quad Ar \overset{\vdots}{\curlywedge} COOR_5 \quad OH \qquad (XVII)$$

in which Ar and $R_5$ are defined as above and Ph represents an optionally substituted phenyl radical.

Generally, the hydrogenolysis is carried out by means of hydrogen in the presence of a catalyst. More particularly, palladium on carbon containing 1 to 10% by weight of palladium or palladium dihydroxide containing 20% by weight of palladium is used as catalyst.

The hydrogenolysis is carried out in an organic solvent or in a mixture of organic solvents. It is advantageous to carry out the procedure in acetic acid optionally combined with an aliphatic alcohol containing 1 to 4 carbon atoms such as a mixture of acetic acid-methanol at a temperature of between 20° and 80° C.

The hydrogen necessary for the hydrogenolysis can also be provided by a compound which liberates hydrogen by chemical reaction or by thermal decomposition (ammonium formate). It is advantageous to carry out the procedure at a hydrogen pressure of between 1 and 50 bar.

The product of general formula (XVII) can be obtained by hydrolysis or alcoholysis of a product of general formula:

$$(XVIII)$$

in which Ar and Ph are defined as above.

It is particularly advantageous to carry out an alcoholysis by means of an alcohol of formula $R_5$—OH in which $R_5$ is defined as above, the procedure being carried out in acidic medium.

Preferably, the alcoholysis is carried out by means of methanol in the presence of a strong inorganic acid such as hydrochloric acid at a temperature close to the reflux temperature of the reaction mixture.

The product of general formula (XVIII) can be obtained by saponification of an ester of general formula:

$$(XIX)$$

in which Ar and Ph are defined as above and $R_8$ represents an alkyl, phenylalkyl or phenyl radical, followed by separation of the 3R, 4S diastereoisomer of general formula (XVII) from the other diastereoisomers.

Generally, the saponification is carried out by means of an inorganic or organic base such as ammonium hydroxide, lithium hydroxide, sodium hydroxide or potassium hydroxide in a suitable solvent such as a methanol-water or tetrahydrofuran-water mixture at a temperature of between −10° C. and 20° C.

The separation of the 3R, 4S diastereoisomer can be carried out by selective crystallization from a suitable organic solvent such as ethyl acetate.

The product of general formula (XIX) can be obtained by cycloaddition of an imine of general formula:

$$(XX)$$

in which Ar and Ph are defined as above, onto an acid halide of general formula:

$$R_8-CO-O \diagdown \qquad (XXI)$$

in which $R_8$ is defined as above and Y represents a halogen atom such as a bromine or chlorine atom.

Generally, the reaction is carried out at a temperature of between 0° and 50° C. in the presence of a base chosen from aliphatic tertiary amines (triethylamine) or pyridine in an organic solvent chosen from optionally halogenated aliphatic hydrocarbons (methylene chloride or chloroform) and aromatic hydrocarbons (benzene, toluene or xylenes).

The product of general formula (XX) can be obtained under conditions analogous to those described by M. Furukawa et al., Chem. Pharm. Bull., 25 (1), 181–184 (1977).

The product of general formula (VI) can be obtained by the action of an alkali metal halide (sodium iodide or potassium fluoride) or an alkali metal azide (sodium azide) or a quaternary ammonium salt or an alkali metal phosphate, on a baccatin III or 10-deacetylbaccatin III derivative of general formula:

$$(XXII)$$

in which $G_1$ is defined as above.

Generally, the reaction is carried out in an organic solvent chosen from ethers (tetrahydrofuran, diisopropyl ether, methyl t-butyl ether) and nitriles (acetonitrile), alone or in the form of a mixture, at a temperature of between 20° C. and the boiling temperature of the reaction mixture.

The product of formula (XXII) in which $G_1$ represents a hydrogen atom or an acetyl, alkoxyacetyl or alkyl radical can be obtained by the action of a trifluoromethanesulphonic acid derivative such as the anhydride or N-phenyltrifluoromethanesulphonimide, on baccatin III or 10-deacetylbaccatin III, which can be extracted according to known methods from yew leaves (Taxus baccata), optionally followed by protection in position 10, it being understood that in order to obtain a product of general formula (XXII) in which $G_1$ represents an alkoxyacetyl or alkyl radical, it is necessary to treat beforehand the 10-deacetylbaccatin III protected in position 7, preferably with a silylated radical, with an alkoxy acetic acid halide or with an alkyl halide.

Generally, the reaction of a trifluoromethanesulphonic acid derivative is carried out in an inert organic solvent (optionally halogenated aliphatic hydrocarbons, or aromatic hydrocarbons) in the presence of an organic base such as an aliphatic tertiary amine (triethylamine) or pyridine, at a temperature of between −50° and +20° C.

Generally, the introduction of an alkoxyacetyl group is carried out by treating the protected 10-deacetylbaccatin III with an alkoxyacetic acid halide, the procedure being carried out in a basic organic solvent such as pyridine at a temperature close to 20° C.

Generally, the introduction of an alkyl radical is carried out by treating the 10-deacetylbaccatin III, protected and metallized in position 10, by means, for example, of an alkali metal hydride (sodium hydride) or a metallic alkylide (butyllithium), with an alkyl halide.

2) by the action of an alkali metal halide (sodium iodide or potassium fluoride) or an alkali metal azide (sodium azide) or a quaternary ammonium salt or an alkali metal phosphate on a product of general formula:

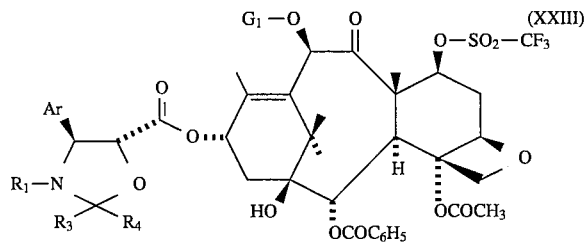

(XXIII)

in which Ar, $R_1$, $R_3$, $R_4$ and $G_1$ are defined as above.

Generally, the reaction is carried out in an organic solvent chosen from ethers (tetrahydrofuran, diisopropyl ether or methyl t-butyl ether) and nitriles (acetonitrile), alone or in the form of a mixture, at a temperature of between 20° C. and the boiling temperature of the reaction mixture.

The product of general formula (XXIII) can be obtained by the action of a trifluoromethanesulphonic acid derivative such as the anhydride or N-phenyltrifluoromethanesulphonimide on a taxoid of general formula:

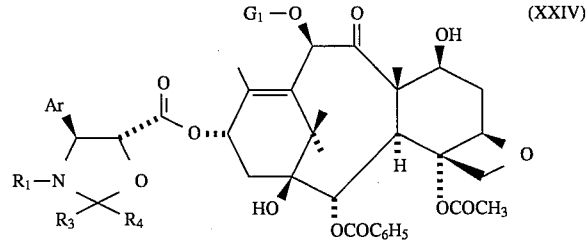

(XXIV)

in which Ar, $R_1$, $R_3$, $R_4$ and $G_1$ are defined as above.

Generally, the reaction is carried out in an inert organic solvent (optionally halogenated aliphatic hydrocarbons, or aromatic hydrocarbons) in the presence of an organic base such as an aliphatic tertiary amine (triethylamine) or pyridine, at a temperature of between −50° and +20° C.

The taxoid of general formula (XXIV), in which $G_1$ represents a hydrogen atom or an acetyl radical, can be obtained from a product of general formula:

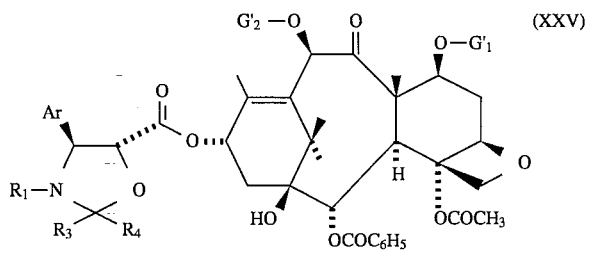

(XXV)

in which Ar, $R_1$, $R_3$ and $R_4$ are defined as above, $G'_1$ represents a hydroxy-protecting group and $G'_2$ represents an acetyl, alkoxyacetyl or alkyl radical or a hydroxy-protecting group, by replacement of the protecting groups $G'_1$ and optionally $G'_2$ by hydrogen atoms.

The radicals $G'_1$ and $G'_2$, when they represent a hydroxy-protecting group, are preferably 2,2,2-trichloroethoxycarbonyl or 2-(2-trichloromethylpropoxy)carbonyl radicals or trialkylsilyl, dialkylarylsilyl, alkyldiarylsilyl or triarylsilyl radicals in which the alkyl portions contain 1 to 4 carbon atoms and the aryl portions are preferably phenyl radicals, it being possible, in addition, for $G'_2$ to represent an alkoxyacetyl radical.

When $G'_1$ and $G'_2$ represent a 2,2,2-trichloroethoxycarbonyl or 2-(2-trichloromethylpropoxy)carbonyl radical, the replacement of the protecting groups by hydrogen atoms is carried out using zinc, optionally combined with copper, in the presence of acetic acid at a temperature of between 20° and 60° C. or by means of an inorganic or organic acid such as hydrochloric acid or acetic acid in solution in an aliphatic alcohol containing 1 to 3 carbon atoms or an aliphatic ester such as ethyl acetate, isopropyl acetate or n-butyl acetate in the presence of zinc optionally combined with copper.

When $G'_1$ represents a silylated radical and $G'_2$ represents an acetyl, alkoxyacetyl or alkyl radical, the replacement of the protecting group $G'_1$ by a hydrogen atom can be carried out by means of, for example, gaseous hydrochloric acid in ethanolic solution at a temperature close to 0° C., under conditions which are without effect on the rest of the molecule.

When $G'_2$ represents an alkoxyacetyl radical, its optional replacement by a hydrogen atom is carried out by treatment in alkaline medium or by the action of a zinc halide under conditions which do not affect the rest of the molecule. Generally, the alkaline treatment is carried out by the action of ammonia in aqueous-alcoholic medium, at a temperature close to 20° C. Generally, the treatment with a zinc halide, preferably zinc iodide, is carried out in methanol at a temperature close to 20° C.

The product of general formula (XXV) can be obtained under the conditions described in international application PCT/WO 9209589.

The new derivatives of general formula (I) can also be obtained by esterification of a product of general formula (VI) by means of an acid of general formula:

(XXVI)

in which Ar and $R_1$ are defined as above and $G_3$ represents a hydroxy-protecting group chosen from methoxymethyl, 1-ethoxyethyl, benzyloxymethyl, (β-trimethylsilyloxy)methyl, tetrahydropyranyl, 2,2,2-trichloroethoxymethyl, 2,2,2-trichloroethoxycarbonyl or 2-(2-trichloromethylpropoxy)carbonyl radicals or $CH_2$—Ph radicals in which Ph represents a phenyl radical optionally substituted by one or more atoms or radicals, which are identical or different, chosen from halogen atoms and alkyl radicals containing 1 to 4 carbon atoms or alkoxy radicals containing 1 to 4 carbon atoms, or an activated derivative of this acid, to give a product of general formula:

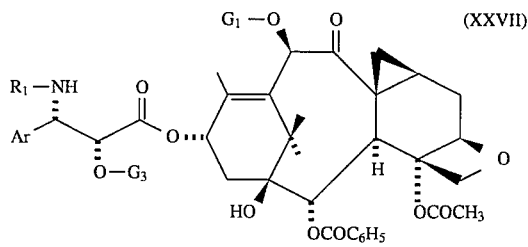

in which Ar, $R_1$, $G_1$, $G_2$ and $G_3$ are defined as above, followed by the replacement of the protecting groups $G_1$, $G_2$ and $G_3$ by hydrogen atoms to give a product of general formula (I).

The esterification can be performed under the conditions described above for the esterification of the product of general formula (VI) by means of an acid of general formula (VII).

The replacement of the protecting groups $G_1$ and $G_3$ of the product of general formula (XXVII) by a hydrogen atom is carried out by treatment with zinc, optionally combined with copper, in the presence of acetic acid at a temperature of between 30° and 60° C. or by means of an inorganic or organic acid such as hydrochloric acid or acetic acid in solution in an aliphatic alcohol containing 1 to 3 carbon atoms or an aliphatic ester such as ethyl acetate, isopropyl acetate or n-butyl acetate in the presence of zinc optionally combined with copper, when $G_1$ and $G_3$ represent a 2,2,2-trichloroethoxycarbonyl or 2-(2-trichloromethylpropoxy)carbonyl radical. The replacement of the protecting group $G_3$, when it represents a silylated radical or an acetal residue, can be carried out by treatment in acidic medium such as for example hydrochloric acid in solution in an aliphatic alcohol containing 1 to 3 carbon atoms (methanol, ethanol, propanol or isopropanol) or aqueous hydrofluoric acid at a temperature of between 0° and 40° C., when it represents an acetal residue, the replacement of the protecting group $G_1$ then being carried out under the conditions described above. When $G_3$ represents a group $-CH_2-Ph$, the replacement of this protecting group with a hydrogen atom can be carried out by hydrogenolysis in the presence of a catalyst.

The acid of general formula (XXVI) can be obtained by saponification of an ester of general formula:

in which Ar, $R_1$, $R_5$ and $G_3$ are defined as above.

Generally, the saponification is carried out by means of an inorganic base (alkali metal hydroxide, carbonate or bicarbonate) in aqueous-alcoholic medium (methanol-water) at a temperature of between 10° and 40° C.

The ester of general formula (XXVIII) can be obtained according to the usual methods for the preparation of ethers, and more particularly according to the procedures described by J-N. DENIS et al., J. Org. Chem., 51, 46–50 (1986), from a product of general formula (XI).

The new products of general formula (I) obtained using the procedures according to the invention can be purified according to known methods such as crystallization or chromatography.

The products of general formula (I) have remarkable biological properties.

In vitro, measurement of the biological activity is carried out on tubulin extracted from pig brain by the method of M. L. Shelanski et al. Proc. Natl. Acad. Sci. USA, 70, 765–768 (1973). The study of the depolymerization of the microtubules into tubulin is carried out according to the method of G. Chauvière et al., C. R. Acad. Sci., 293, série II, 501–503 (1981). In this study, the products of general formula (I) proved at least as active as taxol and Taxotere.

In vivo, the products of general formula (I) proved active in mice grafted with the B16 melanoma at doses of between 1 and 10 mg/kg intraperitoneally, as well as on other liquid or solid tumours.

The new compounds have anti-tumor properties, more particularly, activity against tumors which are resistant to Taxol® and Taxotere®. Such tumors include, for example, colon tumors which have an elevated expression of mdr 1 gene (multi-drug resistant gene). Multi-drug resistance is the usual term relating to the resistance by a tumor against various compounds having differing structures and mechanisms of action. Taxoids are generally known to be highly recognized by experimental tumors such as P388/DOX, a P388 murine leukemia cell line selected for doxorubicin (DOX) resistance, which express mdr 1. The new compounds according to the present invention are less recognized by P388/DOX. More particularly, the new compounds are less recognized than Taxotere® by mdr 1.

In particular, it has been found that the new compounds of the present invention including the compounds of example 1, example 2 and example 3 have better multi-drug resistance properties than Taxol® and Taxotere®. Additionally it has surprisingly been found that the compound of example 3 has substantially better multi-drug resistance properties than the compounds of example 1 and example 2.

The following examples illustrate the present invention.

EXAMPLE 1

A solution of 2.01 g of 4-acetoxy-2α-benzoyloxy-5β,20-epoxy-1β,10β-dihydroxy-7β,8β-methylene-9-oxo-19-nor-11-taxen-13α-yl (4S,5R)-3-tertbutoxycarbonyl-2,2-dimethyl-4-phenyl-5-oxazolidinecarboxylate in 20 cm³ of formic acid is stirred for 4 hours at a temperature close to 20° C. and then concentrated to dryness under reduced pressure (0.27 kPa) at 40° C. The foam obtained is dissolved in 100 cm³ of dichloromethane and the solution obtained is supplemented with 20 cm³ of a saturated aqueous sodium hydrogen carbonate solution. The aqueous phase is separated after settling has taken place and extracted with 20 cm³ of dichloromethane. The organic phases are pooled, dried over magnesium sulphate, filtered and then concentrated to dryness under reduced pressure (2.7 kPa) at 40° C. 1.95 g of a white foam are obtained which are purified by chromatography on 200 g of silica (0.063–0.2 mm) contained in a column 7 cm in diameter, eluting with a dichloromethane-methanol mixture (98-2 by volume) and collecting 30 cm³ fractions. The fractions containing only the desired product are pooled and concentrated to dryness under reduced pressure (0.27 kPa) at 40° C. for 2 hours. 1.57 g of 4-acetoxy-2α-benzoyloxy-5β,20-epoxy-1β,10β-dihydroxy-7β,8β-methylene-9-oxo-19-nor-11-taxen-13α-yl (2R,3S)-3-amino-2-hydroxy-3-phenylpropionate are obtained in the form of a white foam.

To a solution of 400 mg of 4-acetoxy-2α-benzoyloxy-5β,20-epoxy-1β,10β-dihydroxy-7β,8β-methylene-9-oxo-19-nor-11-taxen-13α-yl (2R,3S)-3-amino-2-hydroxy-3-phenylpropionate in 1 cm³ of dichloromethane, kept under an argon atmosphere, are added 60 mg of sodium hydrogen carbonate and then, dropwise, at a temperature close to 20° C., a solution of 0.16 g of di-tert-butyl dicarbonate in 1 cm³ of dichloromethane. The solution obtained is stirred for 64 hours at a temperature close to 20° C. and then supplemented with a mixture of 5 cm³ of distilled water and 10 cm³ of dichloromethane. The organic phase is washed with three times 2 cm³ of distilled water. The organic phase is dried over magnesium sulphate, filtered and then concentrated to dryness under reduced pressure (2.7 kPa) at 40° C. 317 mg of a white foam are thus obtained which are purified by chromatography on 30 g of silica (0.063–0.2 mm) contained in a column 3 cm in diameter, eluting with a dichloromethane-methanol mixture (95-5 by volume) and collecting 5 cm³ fractions. The fractions containing only the desired product are pooled and concentrated to dryness under reduced pressure (0.27 kPa) at 40° C. for 2 hours. 161 mg of 4-acetoxy-2α-benzoyloxy-5β,20-epoxy-1β,10β-dihydroxy-7β,8β-methylene-9-oxo-19-nor-11-taxen-13α-yl (2R, 3S)-3-tert-butoxycarbonylamino-2-hydroxy-3-phenylpropionate are thus obtained in the form of a white foam whose characteristics are the following:

specific rotation: $[\alpha]_D^{20}=-17°$ (c=0.482; methanol)

proton NMR spectrum: (400 MHz; CDCl₃; temperature of 323K; δ in ppm; coupling constants J in Hz):1.21 (s, 3H: —C$\underline{H}_3$ 16 or 17); 1.28 (s, 3H: —C$\underline{H}_3$ 16 or 17); 1.34 [s, 9H: —C(C$\underline{H}_3$)₃]; from 1.30 to 1.50 (mt, 1H: —$\underline{H}$7); 1.80 and 2.36 (2mt, 1H each: —C$\underline{H}_2$—of cyclopropane); 1.88 (s, 3H: —C$\underline{H}_3$ 18); 2.13 [mt, 1H: —(CH)—$\underline{H}$ 6]; 2.26 [dd, 1H, J=15 to 8.5: —(CH)—$\underline{H}$ 14]; 2.35 (s, 3H: —COC$\underline{H}_3$); from 2.35 to 2.50 [mt, 2H: —(CH)—$\underline{H}$ 14 and —(CH)—$\underline{H}$ 6]; 3.21 (d, 1H, J=4: —O$\underline{H}$ 2'); 4.08 [d, 1H, J=8: —(CH)—$\underline{H}$ 20]; 4.16 (d, 1H, J=7: —$\underline{H}$ 3); 4.18 (s, 1H, —O$\underline{H}$ 10); 4.31 [d, 1H, J=8: —(CH)—$\underline{H}$ 20]; 4.61 (dd, 1H, J=4 and 2: —$\underline{H}$ 2'); 4.74 (d, 1H, J=4: —$\underline{H}$ 5); 5.00 (s, 1H: —$\underline{H}$ 10); 5.26 (dd, 1H, J=9 and 2: —$\underline{H}$ 3'); 5.33 (d, 1H, J=9: —N$\underline{H}$ 3'); 5.69 (d, 1H, J=7: —$\underline{H}$ 2); 6.29 (d, 1H, J=8.5: —$\underline{H}$ 13); from 7.30 to 7.50 [mt, 5H: —C₆$\underline{H}_3$ in 3' (—$\underline{H}$ 2 to —$\underline{H}$ 6); 7.51 [t, 2H, J=7.5: —OCOC₆$\underline{H}_3$ (—$\underline{H}$ 3 and $\underline{H}$ 5)]; 7.60 [t, 1H, J=7.5: —OCOC₆$\underline{H}_3$ (—$\underline{H}$ 4)]; 8.14 [d, 2H, J=7.5: —OCOC₆$\underline{H}_3$ (—$\underline{H}$ 2 and $\underline{H}$ 6)].

The 4-acetoxy-2α-benzoyloxy-5β,20-epoxy-1β,10β-dihydroxy-7β,8β-methylene-9-oxo-19-nor-11-taxen-13α-yl (4S,5R)-3-tert-butoxycarbonyl-2,2-dimethyl-4-phenyl-5-oxazolidinecarboxylate can be prepared in the following manner:

To a solution of 2.5 g of 4-acetoxy-2α-benzoyloxy-5β, 20-epoxy-1β,10β-dihydroxy-9-oxo-7β-trifluoromethanesulphonate-11-taxen-13α-yl (4S,5R)-3-tert-butoxycarbonyl-2,2-dimethyl-4-phenyl-5-oxazolidinecarboxylate in 25 cm³ of anhydrous acetonitrile and 3 cm³ of anhydrous tetrahydrofuran, kept under an argon atmosphere, are added 2.5 g of sodium azide. The reaction mixture is heated for 2 hours, with stirring and under an argon atmosphere at a temperature close to 80° C., then cooled to a temperature close to 20° C. and supplemented with 30 cm³ of distilled water. The aqueous phase is separated by decantation and then extracted with 20 cm³ of dichloromethane. The combined organic phases are dried over magnesium sulphate, filtered and then concentrated to dryness under reduced pressure (2.7 kPa) at 40° C. 2.44 g of a yellow foam are thus obtained which are purified by chromatography on 300 g of silica (0.063–0.2 mm) contained in a column 8 cm in diameter, eluting with a dichloromethane-ethyl acetate mixture (90-10 by volume) and collecting 60 cm³ fractions. Fractions 47 to 70 are pooled and concentrated to dryness under reduced pressure (0.27 kPa) at 40° C. for 2 hours. 2.01 g of 4-acetoxy-2α-benzoyloxy-5β,20-epoxy-1β,10β-dihydroxy-7β,8β-methylene-9-oxo-19-nor-11-taxen-13α-yl (4S,5R)-3-tert-butoxycarbonyl-2,2-dimethyl-4-phenyl-5-oxazolidinecarboxylate are thus obtained in the form of a white foam.

The 4-acetoxy-2α-benzoyloxy-5β,20-epoxy-1β,10β-dihydroxy-9-oxo-7β-trifluoromethanesulphonate-11-taxen-13α-yl (4S,5R)-3-tert-butoxycarbonyl-2,2-dimethyl-4-phenyl-5-oxazolidinecarboxylate can be prepared in the following manner:

To a solution of 2.86 g of 4-acetoxy-2α-benzoyloxy-5β, 20-epoxy-1β,7β,10β-trihydroxy-9-oxo-11-taxen-13α-yl (4S,5R)-3-tert-butoxycarbonyl-2,2-dimethyl-4-phenyl-5-oxazolidinecarboxylate in 29 cm³ of anhydrous dichloromethane, kept under an argon atmosphere, are added 0.955 cm³ of pyridine and 50 mg of powdered activated 4 Å molecular sieve. The reaction mixture is cooled to a temperature close to −35° C., slowly supplemented with 0.85 cm³ of trifluoromethanesulphonic anhydride, stirred at a temperature close to −5° C. for 15 minutes and supplemented with 10 cm³ of distilled water. After filtration on sintered glass provided with celite and rinsing off the sintered glass with 3 times 10 cm³ of a methanol-dichloromethane mixture (10-90 by volume), the aqueous phase is separated after settling has taken place and extracted with twice 10 cm³ of dichloromethane. The organic phases are pooled, dried over magnesium sulphate, filtered and then concentrated to dryness under reduced pressure (2.7 kPa) at 40° C. 3.87 g of a white foam are obtained which are purified by chromatography on 400 g of silica (0.063–0.2 mm) contained in a column 10 cm in diameter, eluting with a dichloromethane-ethyl acetate gradient (from 97.5-2.5 to 90-10 by volume) and collecting 80 cm³ fractions. The fractions containing only the desired product are pooled and concentrated to dryness under reduced pressure (0.27 kPa) at 40° C. for 2 hours. 3.0 g of 4-acetoxy-2α-benzoyloxy-5β, 20-epoxy-1β,10β-dihydroxy-9-oxo-7β-trifluoromethanesulphonate-11-taxen-13α-yl (4S,5R)-3-tert-butoxycarbonyl-2,2-dimethyl-4-phenyl-5-oxazolidinecarboxylate are thus obtained in the form of a white foam.

The 4-acetoxy-2α-benzoyloxy-5β,20-epoxy-1β,7β,10β-trihydroxy-9-oxo-11-taxen-13α-yl (4S,5R)-3-tart-butoxycarbonyl-2,2-dimethyl-4-phenyl-5-oxazolidinecarboxylate can be prepared in the following manner:

A solution of 24.35 g of 4-acetoxy-2α-benzoyloxy-5β, 20-epoxy-9-oxo-7β,10β-[bis(2,2,2-trichloroethoxy)carbonyloxy]-1β-hydroxy-11-taxen-13α-yl (4S,5R)-3-tert-butoxycarbonyl-2,2-dimethyl-4-phenyl-5-oxazolidinecarboxylate in a mixture of 130 cm³ of ethyl acetate and 46.5 cm³ of acetic acid is heated, with stirring and under an argon atmosphere up to a temperature close to 60° C. and then supplemented with 40 g of zinc powder. The reaction mixture is then stirred for 30 minutes at 60° C. and then cooled to a temperature close to 20° C. and filtered on sintered glass provided with celite. The sintered glass is washed with 100 cm³ of a methanol-dichloromethane mixture (20-80 by volume); the filtrates are pooled and then concentrated to dryness under reduced pressure (0.27 kPa) at a temperature close to 40° C.

The residue is supplemented with 500 cm³ of dichloromethane. The organic phase is washed with twice 50 cm³ of a saturated aqueous sodium hydrogen carbonate solution and then with 50 cm³ of distilled water. The aqueous phases obtained after settling has taken place and pooled are extracted with twice 30 cm³ of dichloromethane. The organic phases are pooled, dried over magnesium sulphate, filtered and then concentrated to dryness under reduced pressure (2.7 kPa) at 40° C. 19.7 g of a white foam are obtained which are purified by chromatography on 800 g of silica (0.063–0.2 mm) contained in a column 10 cm in diameter, eluting with a dichloromethane-methanol gradient (from 100-0 to 97-3 by volume) and collecting 80 cm³ fractions. The fractions containing only the desired product are pooled and concentrated to dryness under reduced pressure (0.27 kPa) at 40° C. for 2 hours. 16.53 g of 4-acetoxy-2α-benzoyloxy-5β,20-epoxy-1β,7β, 10β-trihydroxy-9-oxo-11-taxen-13α-yl (4S,5R)-3-tert-butoxycarbonyl-2,2-dimethyl-4-phenyl-5-oxazolidinecarboxylate in the form of a white foam.

The 4-acetoxy-2β-benzoyloxy-5β,20-epoxy-9-oxo-7β, 10β-[bis(2,2,2-trichloroethoxy)carbonyloxy]-1β-hydroxy-11-taken-13α-yl (4S,5R)-3-tert-butoxycarbonyl-2,2-dimethyl-4-phenyl-5-oxazolidinecarboxylate can be prepared according to the method described in international application PCT WO 9209589.

EXAMPLE 2

To a solution of 550 mg of 4α,10β-diacetoxy-2α-benzoyloxy-5β,20-epoxy-1β-hydroxy-7β,8β-methylene-9-oxo-19-nor-11-taxen-13α-yl (2R,3S)-3-amino-2-hydroxy-3-phenylpropionate are added 45 cm³ of distilled water, 45cm³ of a saturated aqueous sodium hydrogen carbonate solution and then, dropwise, at a temperature close to 20° C., 0.096 cm³ of benzoyl chloride. The mixture obtained is stirred for 10 minutes at a temperature close to 20° C. After settling has taken place, the aqueous phase is extracted with twice 30 cm³ of ethyl acetate. The combined organic phases are dried over magnesium sulphate, filtered and then concentrated to dryness under reduced pressure (2.7 kPa) at 40° C. 670 mg of a white foam are thus obtained which are purified by chromatography at atmospheric pressure on 50 g of silica (0.063–0.2 mm) contained in a column 2.5 cm in diameter, eluting with a methanol-dichloromethane mixture (1-99 then 2.5-97.5 by volume) and collecting 10 cm³ fractions. The fractions containing only the desired product are pooled and concentrated to dryness under reduced pressure (2.7 kPa) at 40° C. 610 mg of a white foam are thus obtained. A sample of 300 mg is purified by preparative chromatography on 12 thin-layer silica plates (Kieselgel 60F254, Merck; thickness 0.25 mm), eluting with a methanol-dichloromethane mixture (3-97 by volume). After elution of the zone corresponding to the main product with a methanol-dichloromethane mixture (10-90 by volume) and then evaporation of the solvents under reduced pressure (0.27 kPa) at a temperature close to 40° C., 155.2 mg of 4α,10β-diacetoxy-2α-benzoyloxy-5β, 20-epoxy-1β-hydroxy-7β, 8β-methylene-9-oxo-19-nor-11-taxen-13α-yl (2R, 3S)-3-benzoylamino-2-hydroxy-3-phenylpropionate are obtained in the foam of a white foam whose characteristics are the following:

specific rotation: $[\alpha]_D^{20}$=−30.5° (c=0.491; methanol)

proton NMR spectrum: (300 MHz; CDCl₃; δ in ppm; coupling constants J in Hz):1.27 (s, 3H: —C$\underline{H}_3$ 16 and 17); 1.30 (s, 3H: —C$\underline{H}_3$ 16 or 17); 1.40 (mt, 1H: —$\underline{H}$7); 1.62 and 2.25 (q and m, 1H each: C$\underline{H}_2$— of cyclopropane); 1.85 (s, 3H: —C$\underline{H}_3$ 18); 1.96 (s, 1H: —O$\underline{H}$ in 1); 2.05 and 2.48 (d and m, 1H each: —C$\underline{H}_3$— in 6); 2.24 (s, 3H: —COC$\underline{H}_3$ in 10); 2.28 and 2.50 (m, 1H each: —C$\underline{H}_3$ in 14); 2.45 (s, 3H: —COC$\underline{H}_3$ in 4); 3.52 (d, 1H: —O$\underline{H}$ in 2'); 4.10 and 4.35 (d, 1H each: —C$\underline{H}_3$ in 20); 4.11 (d, 1H: —$\underline{H}$3); 4.77 (broad d, 1H: —$\underline{H}$5); 4.82 (dd, 1H: —$\underline{H}$2'); 5.70 (d, 1H: —$\underline{H}$ in 2); 5.84 (dd, 1H: —$\underline{H}$3'); 6.30 (broad t, 1H: —$\underline{H}$13); 6.36 (s, 1H: —$\underline{H}$10); 7.00 (d, 1H: —CON$\underline{H}$—); from 7.35 to 8.30 (m, 15H: —C₆$\underline{H}_5$ in 3', —OCOC₆$\underline{H}_5$ and NHCOC₆$\underline{H}_5$).

The 4α,10β-diacetoxy-2α-benzoyloxy-5β, 20-epoxy-1β-hydroxy-7β, 8β-methylene-9-oxo-19-nor-11-taxen-13α-yl (2R, 3S)-3-amino-2-hydroxy-3-phenylpropionate can be prepared by carrying out the procedure under the conditions described in Example 1 for the preparation of 4-acetoxy-2α-benzoyloxy-5β,20-epoxy-1β,10β-dihydroxy-7β, 8β-methylene-9-oxo-19-nor-11-taxen-13α-yl (2R, 3S)-3-amino-2-hydroxy-3-phenylpropionate. Thus, starting with 1.6 g of 4α,10β-diacetoxy-2α-benzoyloxy-5β,20-epoxy-1β-hydroxy-7β, 8β-methylene-9-oxo-19-nor-11-taxen-13α-yl (4S, 5R)-3-tert-butoxycarbonyl-2,2-dimethyl-4-phenyl-5-oxazolidincarboxylate, 1.14 g of 4β,10β-diacetoxy-2α-benzoyloxy-5β,20-epoxy-1β-hydroxy-7β,8β-methylene-9-oxo-19-nor-11-taxen-13α-yl are obtained in the form of a white foam.

The 4α,10β-diacetoxy-2α-benzoyloxy-5β,20-epoxy-1β-hydroxy-7β,8β-methylene-9-oxo-19-nor-11-taxen-13α-yl (4S, 5R)-3-tert-butoxycarbonyl-2,2-dimethyl-4-phenyl-5-oxazolidincarboxylate can be prepared under the conditions described in Example 1 for the preparation of 4α-acetoxy-2α-benzoyloxy-5β, 20-epoxy-1β,10β-dihydroxy-7β,8β-methylene-9-oxo-19-nor-11-taxen-13α-yl (4S, 5R)-3-tert-butoxycarbonyl-2,2-dimethyl-4-phenyl-5-oxazolidinecarboxylate. Thus, starting with 2.2 g of 4α, 10β-diacetoxy-2α-benzoyloxy-5β, 20-epoxy-1β-hydroxy-9-oxo-7β-trifluoromethanesulphonate-11-taxen-13α-yl (4S, 5R)-3-tert-butoxycarbonyl-2,2-dimethyl-4-phenyl-5-oxazolidincarboxylate, 1.62 g of 4α, 10β-diacetoxy-2α-benzoyloxy-5β,20-epoxy-1β-hydroxy-7β,8β-methylene-9-oxo-19-nor-11-taxen-13α-yl (4S,5S)-3-tert-butoxycarbonyl-2,2-dimethyl-4-phenyl-5-oxazolidincarboxylate are obtained in the form of a white foam.

The 4α,10β-diacetoxy-2α-benzoyloxy-5β,20-epoxy-1β-hydroxy-9-oxo-7β-trifluoromethanesulphonate-11-taxen-13αyl (4S,5R)-3-tert-butoxycarbonyl-2,2-dimethyl-4-phenyl-5-oxazolidincarboxylate can be prepared under the conditions described in Example 1 for the preparation of 4α-acetoxy-2α-benzoyloxy-5β,20-epoxy-1β,10β-dihydroxy-9-oxo-7β-trifluoromethanesulphonate-19-nor-11-taxen-13α-yl (4S,5R)-3-tert-butoxycarbonyl-2,2-dimethyl-4-phenyl-5-oxazolidincarboxylate. Thus, starting with 2.4 g of 4α,10β-diacetoxy-2α-benzoyloxy-5β,20-epoxy-1β,7β-dihydroxy-9-oxo-11-taxen-13α-yl (4S,5R)-3-tert-butoxycarbonyl-2,2-dimethyl-4-phenyl-5-oxazolidincarboxylate, 2.46 g of 4α,10β-diacetoxy-2α-benzoyloxy-5β,20-epoxy-1β-hydroxy-9-oxo-7β-trifluoromethanesulphonate-11-taxen-13α-yl (4S,5R)-3-tert-butoxycarbonyl-2,2-dimethyl-4-phenyl-5-oxazolidincarboxylate are obtained in the form of a white foam.

The 4α,10β-diacetoxy-2α-benzoyloxy-5β,20-epoxy-1β, 7β-dihydroxy-9-oxo-11-taxen-13α-yl (4S,5R)-3-tert-butoxycarbonyl-2,2-dimethyl-4-phenyl-5-oxazolidincarboxylate can be prepared under the conditions described in International Application PCT WO 9209589.

EXAMPLE 3

To a solution of 550 mg of 4α,10β-diacetoxy-2α-benzoyloxy-5β,20-epoxy-1β-hydroxy-7β,8β-methylene-9-oxo-19-nor-11-taxen-13α-yl (2R,3S)-3-amino-2-hydroxy-3-phenylpropionate in 1 cm³ of dichloromethane, kept under an argon atmosphere, are added 76 mg of sodium hydrogen carbonate and then, dropwise, at a temperature close to 20° C., a solution of 197 mg of di-tert-butyl dicarbonate in 1 cm³ of dichloromethane. The solution obtained is stirred for 15 hours at a temperature close to 20° C. and then supplemented with a mixture of 5 cm³ of distilled water and 10 cm³ of dichloromethane. The aqueous phase is extracted with 5 cm³ of dichloromethane. The combined organic phases are dried over magnesium sulphate, filtered and then concentrated to dryness under reduced pressure (2.7 kPa) at 40° C. 780 mg of a white foam are thus obtained which are purified by chromatography at atmospheric pressure on 50 g of silica (0.063–0.2 mm) contained in a column 2.5 cm in diameter, eluting with a methanol-dichloromethane mixture (1–99 then 2.5-97.5 by volume) and collecting 10 cm³ fractions. The fractions containing only the desired product are pooled and concentrated to dryness under reduced pressure (2.7 kPa) at 40° C. 660 mg of a white foam are thus obtained. A sample of 300 mg is purified by preparative chromatography on 12 thin-layer silica plates (Kieselgel 60F254, Merck; thickness 0.25 mm), eluting with a methanol-dichloromethane mixture (4–96 by volume). After elution of the zone corresponding to the main product with a methanol-dichloromethane mixture (10-90 by volume) and then evaporation of the solvents under reduced pressure (0.27 kPa) at a temperature close to 40° C., 159.7 mg of 4α,10β-diacetoxy-2α-benzoyloxy-5β,20-epoxy-1β-hydroxy-7β,8β-methylene-9-oxo-19-nor-11-taxen-13α-yl (2R,3S)-3-tert-butoxycarbonylamino-2-hydroxy-3-phenylpropionate are obtained in the form of a white foam whose characteristics are the following:

specific rotation: $[\alpha]_D^{20} = -34°$ (c=0.564; methanol)

proton NMR spectrum: (400 MHz; CDCl₃; δ in ppm; coupling constants J in Hz): 1.28 (s, 3H: —C$\underline{H}_3$ 16 or 17); 1.30 [s, 9H: —C(C$\underline{H}_3$)₃]; 1.38 (mt, 1H: —$\underline{H}$7); 1.60 (s, 3H: —C$\underline{H}_3$ 16 or 17); 1.68 and 2.25 (t and m, 1H each; C$\underline{H}_3$— of cyclopropane); 1.85 (s, 3H: —C$\underline{H}_3$ 18); 2.10 and 2.45 (d and td, 1H each: —C$\underline{H}_3$— in 6); 2.23 (s, 3H: —COC$\underline{H}_3$ in 10); 2.22 and 2.40 (m, 1H each: —C$\underline{H}_2$— in 14); 2.40 (s, 3H: —COC$\underline{H}_3$ in 4); 3.28 (d, 1H: —O$\underline{H}$ in 2'); 4.05 and 4.22 (d, 1H each: —C$\underline{H}_2$— in 20); 4.10 (d, 1H: —$\underline{H}$3); 4.62 (broad s, 1H: —$\underline{H}$2'); 4.73 (d, 1H: —$\underline{H}$5); 5.29 (broad d, 1H: —$\underline{H}$3'); 5.37 (d, 1H: —CON$\underline{H}$—); 5.67 (d, 1H: —$\underline{H}$ in 2); 6.28 (broad t, 1H: —$\underline{H}$13); 6.33 (s, 1H: —$\underline{H}$10); from 7.30 to 7.45 (mt, 5H: —C₆H₅ in 3'); 7.51 [t, 2H: —OCOC₆H₅ (—$\underline{H}$3 and —$\underline{H}$5)]; 7.61 [t, 1H: —OCOC₆H₅ (—$\underline{H}$4)]; 8.17 [d, 2H: —OCOC₆H₅ (—$\underline{H}$2 and —$\underline{H}$6)].

EXAMPLE 4

To a solution of 100 mg of 10-deacetylbaccatin III in a mixture of 3 cm³ of tetrahydrofuran and 0.05 cm³ of pyridine cooled to a temperature close to −78° C. and kept under an argon atmosphere, is added, dropwise, 0.09 cm³ of trifluoromethanesulphonic anhydride. The temperature is allowed to rise slowly to a temperature close to 0° C. over approximately one hour, then up to a temperature close to 20° C. over approximately one hour. After 2 hours at a temperature close to 20° C., 200 mg of tetrabutylammonium iodide are added, then the solution is heated at the boiling temperature of the solvent for 15 hours. After cooling to a temperature close to 20° C., 10 cm³ of ethyl acetate and then 1 cm³ of distilled water are added. After separation after settling has taken place, the organic phase is dried over magnesium sulphate, filtered and concentrated to dryness under reduced pressure (2.7 kPa) at 40° C. 116 mg of a yellow oil are thus obtained which are purified by chromatography at atmospheric pressure on 30 g of silica (0.063-0.2 mm) contained in a column 2.5 cm in diameter, eluting with an ethyl acetate-dichloromethane mixture, with an elution gradient from 0-100 to 80-20 by volume. The fractions containing the desired product are pooled and concentrated to dryness under reduced pressure (0.27 kPa) at 40° C. 10.3 mg of 10-deacetyl-7β,8β-methylene-19-norbaccatin III are thus obtained in the form of a white foam whose characteristics are the following:

proton NMR spectrum: (400 MHz; CDCl₃; δ in ppm; coupling constants J in Hz): 1.14 (s, 3H: —C$\underline{H}_3$ in 16 or 17); 1.42 (mt, 1H: —$\underline{H}$ in 7); 1.76 and 2.31 (t and m, 1H each; C$\underline{H}_2$ of cyclopropane); 2.07 (s, 3H; —C$\underline{H}_3$ in 18); 2.15 and 2.50 (broad d and td, 1H each: C$\underline{H}_2$ — in 6); 2.30 (s, 3H: —COC$\underline{H}_3$ in 4); 2.28 and 2.35 (m, 1H each: —C$\underline{H}_2$ in 14); 4.11 and 4.37 (d, 1H each: —C$\underline{H}_2$ in 20); 4.28 (d, 1H: —$\underline{H}$3 in 3); 4.79 (d, 1H: —$\underline{H}$ in 5); 4.88 (broad t, 1H: —$\underline{H}$ in 13); 5.09 (s, 1H: —$\underline{H}$ in 10); 5.66 (d, 1H: —$\underline{H}$ in 2); 7.51 [t, 2H: —OCOC₆H₅ (—$\underline{H}$ in 3 and 5)]; 7.61 [t, 1H: —OCOC₆H₅ (—$\underline{H}$ in 4)]; 8.17 [d, 2H: —OCOC₆H₅ (—$\underline{H}$ in 2 and 6)].

¹³C NMR spectrum: (100 MHz; CDCl₃; δ in ppm; uncoupled; s=singlet, d=doublet; t=triplet; q=quadruplet): 15 (q, C18); 16.5 (t, C19); 20 and 27 (q, C16 and C17); 22.5 (q, —CO$\underline{C}$H₃); 26.5 (t, C6); 33 (d, C7); 35 (s, C8); 39 (d, C3); 39.5 (t, C14); 43 (s, C15); 68 (d, C13); 76 (t, C20); 76.2 (d, C10); 79.5 (s, C1); 80 (s, C4); 81 (d, C2); 85 (d, C5); 129 (d, C2: —OCOC₆H₅); 130 (s, C1 of —OCOC₆H₅); 130.5 (d, C3 of —OCOC₆H₅); 134 (d, C4 of —OCOC₆H₅); 136 (s, C11); 143 (s, C12); 168 (s, —O$\underline{C}$OC₆H₅); 171 (s, —$\underline{C}$OCH₃); 210 (s, C9).

The new products of general formula (I) manifest a significant inhibitory activity with respect to abnormal cell proliferation and possess therapeutic properties which permit the treatment of patients having pathological conditions associated with abnormal cell proliferation. The pathological conditions include the abnormal cell proliferation of malignant or nonmalignant cells of various tissues and/or organs, comprising, with no limitation being implied, muscle, bone or connective tissues, the skin, brain, lungs, sex organs, the lymphatic or renal systems, mammary or blood cells, liver, the digestive tract, pancreas and thyroid or adrenal glands. These pathological conditions can also include psoriasis, solid tumours, cancers of the ovary, breast, brain, prostate, colon, stomach, kidney or testicles, Kaposi's sarcoma, cholangioma, chorioma, neuroblastoma, Wilms' tumour, Hodgkin's disease, melanomas, multiple myelomas, lymphatic leukaemias and acute or chronic granulocytic lymphomas. The new products according to the invention are particularly useful for the treatment of cancer of the ovary. The products according to the invention can be used to prevent or retard the appearance or reappearance of the pathological conditions or to treat these pathological conditions.

The products according to the invention can be administered to a patient in various forms adapted to the chosen route of administration which is preferably the parenteral route. Paranteral administration comprises intravenous, intraperitoneal, intramuscular or subcutaneous administrations. Intraperitoneal or intravenous administration is more particularly preferred.

The present invention also comprises pharmaceutical compositions containing at least one product of general formula (I) in a sufficient quantity adapted to use in human or veterinary therapy. The compositions can be prepared according to the customary methods, using one or more pharmaceutically acceptable adjuvants, carriers or excipients. Suitable carriers include diluents, sterile aqueous media and various nontoxic solvents. Preferably, the compositions are provided in the form of aqueous solutions or suspensions, of injectable solutions which may contain emulsifying agents, colorants, preservatives or stabilizers.

The choice of adjuvants or excipients may be determined by the solubility and the chemical properties of the product, the particular mode of administration and good pharmaceutical practice.

For parenteral administration, aqueous or nonaqueous sterile solutions or suspensions are used. For the preparation of nonaqueous solutions or suspensions, natural vegetable oils such as olive oil, sesame oil or paraffin oil or injectable organic esters such as ethyl oleats can be used. The aqueous sterile solutions may consist of a solution of a pharmaceutically acceptable salt in solution in water. The aqueous solutions are suitable for intravenous administration in so far as the pH is appropriately adjusted and isotonicity is achieved, for example, with a sufficient quantity of sodium chloride or glucose. The sterilization can be performed by heating or by any other means which does not adversely affect the composition.

It is clearly understood that all the products entering into the compositions according to the invention should be pure and nontoxic for the quantities used.

The compositions may contain at least 0.01% of therapeutically active product. The quantity of active product in a composition is such that a suitable dosage can be prescribed. Preferably, the compositions are prepared such that a single dose contains about 0.01 to 1000 mg of active product for parenteral administration.

The therapeutic treatment can be performed concurrently with other therapeutic treatments including antineoplastic drugs, monoclonal antibodies, immunotherapies or radiotherapies or biological including antineoplastic drugs, monoclonal antibodies, immunotherapies or radiotherapies or biological response modifiers. The response modifiers include, with no limitation being implied, lymphokines and cytokines such as interleukins, interferons ($\alpha$, $\beta$ or $\delta$) and TNF. Other chemotherapeutic agents which are useful in the treatment of disorders caused by abnormal proliferation of cells include, with no limitation being implied, alkylating agents like nitrogen mustards such as mechloretamine, cyclophosphamide, melphalan and chlorambucil, alkyl sulphonates such as busulfan, nitrosoureas such as carmustine, lomustine, semustine and streptozocin, triazenes such as decarbazine, antimetabolites such as folic acid analogues like methotrexate, pyrimidine analogues such as fluorouracil and cytarabine, purine analogues such as mercaptopurine and thioguanine, natural products like vinca alkaloids such as vinblastine, vincristine and vindesine, epipodophyllotoxins such as etoposide and teniposide, antibiotics such as dactinomycin, daunorubicin, doxorubicin, bleomycin, plicamycin and mitomycin, enzymes such as L-asparaginase, various agents such as coordination complexes of platinum like cisplatin, substituted ureas like hydroxyurea, methylhydrazine derivatives such as procarbazine, adrenocortical suppressants such as mitotane and aminoglutethymide, hormones and antagonists such as adrenocorticosteroids such as prednisone, progestins such as hydroxyprogesterone caproate, methoxyprogesterone acetate and megastrol acetate, oestrogens such as diethylstilbestrol and ethynylestradiol, antioestrogens such as tamoxifen, and androgens such as testosterone propionate and fluoxymesterone.

The doses used for carrying out the methods according to the invention are those which permit a prophylactic treatment or a maximum therapeutic response. The doses vary according to the form of administration, the particular product selected and the characteristics specific to the subject to be treated. In general, the doses are those which are therapeutically effective for the treatment of disorders caused by abnormal cell proliferation. The products according to the invention can be administered as often as necessary to obtain the desired therapeutic effect. Some patients may respond rapidly to relatively high or low doses, and then require low or zero maintenance doses. Generally, low doses will be used at the beginning of the treatment and, if necessary, increasingly higher doses will be administered until an optimum effect is obtained. For other patients, it may be necessary to administer maintenance doses 1 to 8 times per day, preferably 1 to 4 times according to the physiological needs of the patient considered. It is also possible that for certain patients it may be necessary to use only one to two daily administrations.

In man, the doses are generally between 0.01 and 200 mg/kg. For intraperitoneal administration, the doses will generally be between 0.1 and 100 mg/kg and, preferably, between 0.5 and 50 mg/kg and, still more specifically, between 1 and 10 mg/kg. For intravenous administration, the doses are generally between 0.1 and 50 mg/kg and, preferably, between 0.1 and 5 mg/kg and, still more specifically, between 1 and 2 mg/kg. It is understood that, in order to choose the most appropriate dosage, account should be taken of the route of administration, the patient's weight, his general state of health, his age and all factors which may influence the efficacy of the treatment.

The following example illustrates a composition according to the invention.

EXAMPLE 40 mg of the product obtained in Example 1 are dissolved in 1 cm³ of Emulphor EL 620 and 1 cm³ of ethanol and then the solution is diluted by addition of 18 cm³ of physiological saline.

The composition is administered by perfusion for 1 hour by introduction into physiological saline.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A process for preparing a taxoid of formula I:

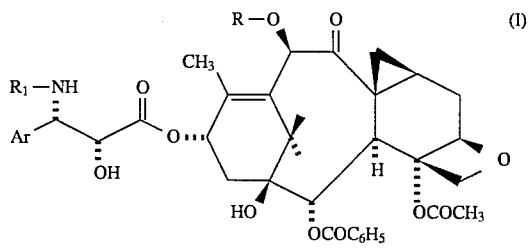

in which R represents a hydrogen atom or an acetyl, alkoxyacetyl or alkyl radical, $R_1$ represents a benzoyl radical or a radical $R_2$—O—CO in which $R_2$ represents an alkyl, alkenyl, alkynyl, cycloalkyl, cycloalkenyl, bicycloalkyl, phenyl or heterocyclyl radical, and Ar represents an aryl radical, comprising the steps of esterifying a compound of formula VI:

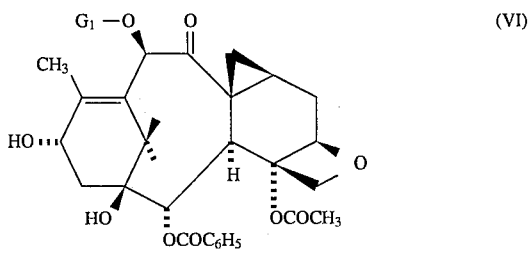

in which $G_1$ represents a hydrogen atom, an acetyl, alkyl, or alkoxyacetyl radical or a hydroxy-protecting group, with a free acid of the formula XXVI:

in which Ar and $R_1$ are as defined above, and $G_3$ represents a hydroxy-protecting group, or of an activated derivative of this acid, to give a compound of the formula XXVII:

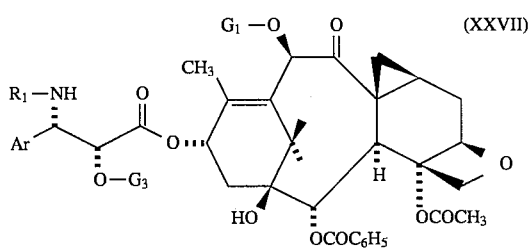

in which Ar, $R_1$, $G_1$ and $G_3$ are as defined above, replacing the protecting group $G_3$ with hydrogen, and when $G_1$ represents a protecting group, removing said $G_1$ protecting group to give a product of formula I.

2. The process of claim 1, wherein the $G_1$ protecting group is replaced by a hydrogen atom.

3. The process of claim 1, wherein the esterifying step further comprises using a condensing agent chosen from carbodiimides and reactive carbonates and an activating agent chosen from aminopyridines in an organic solvent chosen from ethers, ketones, esters, nitriles, aliphatic hydrocarbons, halogenated aliphatic hydrocarbons, and aromatic hydrocarbons at a temperature ranging from −10° to 90° C.

4. The process of claim 1, wherein the free acid of esterifying step is in an anhydride form, and wherein the esterifying step is carried out in the presence of an activating agent chosen from aminopyridines in an organic solvent chosen from ethers, esters, ketones, nitriles, aliphatic hydrocarbons, halogenated aliphatic hydrocarbons, and aromatic hydrocarbons at a temperature ranging from 0° to 90° C.

5. The process of claim 1, wherein the free acid of the esterifying step is in a halide form or an anhydride form with an aliphatic or aromatic acid, and wherein esterifying step is carried out in the presence of a base chosen from tertiary aliphatic amines in an organic solvent chosen from ethers, esters, ketones, nitriles, aliphatic hydrocarbons, halogenated aliphatic hydrocarbons, and aromatic hydrocarbons at a temperature ranging from 0° to 80° C.

6. The process of claim 5, wherein the anhydride form of the free acid is prepared in situ.

7. The process of claim 1, wherein $G_1$ and $G_3$ represent a 2,2,2-trichloroethoxycarbonyl or 2-(2-trichloromethylpropoxy)carbonyl radical and each is replaced a hydrogen atom by treating with zinc or zinc combined with copper in the presence of acetic acid at a temperature ranging from 30° to 60° C. or by treating with an inorganic or organic acid in solution in an aliphatic alcohol containing 1 to 3 carbon atoms or an aliphatic ester in the presence of zinc or zinc combined with copper.

8. The process of claim 1, wherein $G_3$ represents a silylated radical or an acetal residue and is replaced with hydrogen by treating in acidic medium in solution in an aliphatic alcohol containing 1 to 3 carbon atoms or aqueous hydrofluoric acid at a temperature ranging from 0° to 40° C., followed by the replacement of the protecting group $G_1$ with hydrogen by treating with zinc or zinc combined with copper in the presence of acetic acid at a temperature ranging from 30° to 60° C. or by treating with an inorganic or organic acid or acetic acid in solution in an aliphatic alcohol containing 1 to 3 carbon atoms or an aliphatic ester in the presence of zinc or zinc combined with copper.

9. The process of claim 1, wherein $G_1$ represents an alkoxyacetyl radical and is replaced with a hydrogen atom by treating in an alkaline medium using ammonia in aqueous-alcoholic medium at a temperature of about 20° C. or by treating with zinc halide in methanol at a temperature of about 20° C.

10. The process of claim 7, wherein the organic acid is selected from hydrochloric acid and acetic acid.

11. The process of claim 7, wherein the aliphatic ester is selected from ethyl acetate, isopropyl acetate, and n-butyl acetate.

12. The process of claim 8, wherein the organic acid is selected from hydrochloric acid and acetic acid.

13. The process of claim 8, wherein the aliphatic ester is selected from ethyl acetate, isopropyl acetate, and n-butyl acetate.

14. The process of claim 1, wherein when $G_3$ represents a radical —$CH_2$—Ph and is replaced by a hydrogen atom using hydrogenolysis after replacing the protecting group $G_1$.

15. The process for preparing a taxiod of formula I:

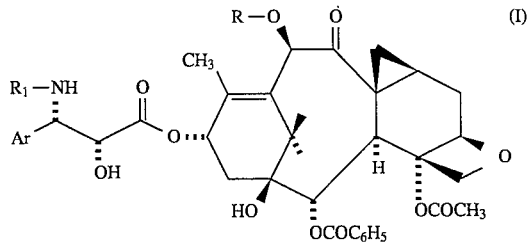

in which R represents a hydrogen atom or an acetyl, alkoxyacetyl or alkyl radical, $R_1$ represents a radical $R_2$—O—CO— in which $R_2$ represents an alkyl radical, and Ar represents an aryl radical, comprising the steps of esterifying a compound of formula VI:

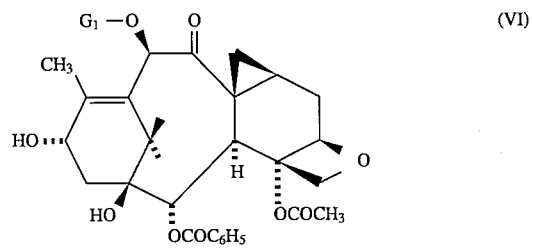

in which $G_1$ represents a hydrogen atom, an acetyl, alkyl, or alkoxyacetyl radical or a hydroxy-protecting group, with a free acid of the formula XXVI:

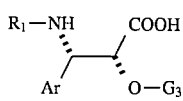

(XXVI)

in which Ar and $R_1$ are as defined above, and $G_3$ represents a hydroxy-protecting group, or an activated derivative of this acid, to give a compound of the formula XXVII:

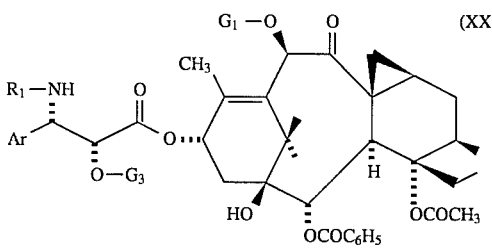

(XXVII)

in which Ar, $R_1$, $G_1$ and $G_3$ are as defined above,
replacing the protecting group $G_3$ with hydrogen, and
when $G_1$ represents a protecting group, removing said $G_1$ protecting group to give a product of formula I.

16. The process of claim 15, wherein the $G_1$ protecting group is replaced by a hydrogen atom.

17. The process of claim 15, wherein the esterifying step further comprises using a condensing agent chosen from carbodiimides and reactive carbonates and an activating agent chosen from aminopyridines in an organic solvent chosen from ethers, ketones, esters, nitriles, aliphatic hydrocarbons, halogenated aliphatic hydrocarbons, and aromatic hydrocarbons at a temperature ranging from $-10°$ to $90°$ C.

18. The process of claim 15, wherein the free acid of esterifying step is in an anhydride form, and wherein the esterifying step is carried out in the presence of an activating agent chosen from aminopyridines in an organic solvent chosen from ethers, esters, ketones, nitriles, aliphatic hydrocarbons, halogenated aliphatic hydrocarbons, and aromatic hydrocarbons at a temperature ranging from $0°$ to $90°$ C.

19. The process of claim 15, wherein the free acid of the esterifying step is in a halide form or an anhydride form with an aliphatic or aromatic acid, and wherein the esterifying step is carried out in the presence of a base chosen from tertiary aliphatic amines in an organic solvent chosen from ethers, esters, ketones, nitriles, aliphatic hydrocarbons, halogenated aliphatic hydrocarbons, and aromatic hydrocarbons at a temperature ranging from $0°$ to $80°$ C.

20. The process of claim 19, wherein the anhydride form of the free acid is prepared in situ.

21. The process of claim 15, wherein $G_1$ and $G_3$ represent a 2,2,2-trichloroethoxycarbonyl or 2-(2-trichloromethylpropoxy)carbonyl radical and each is replaced with a hydrogen atom by treating with zinc or zinc combined with copper in the presence of acetic acid at a temperature ranging from $30°$ to $60°$ C. or by treating with an inorganic or organic acid in solution in an aliphatic alcohol containing 1 to 3 carbon atoms or an aliphatic ester in the presence of zinc or zinc combined with copper.

22. The process of claim 15, wherein $G_3$ represents a silylated radical or an acetal residue and is replaced with hydrogen by treating in acidic medium in solution in an aliphatic alcohol containing 1 to 3 carbon atoms or aqueous hydrofluoric acid at a temperature ranging from $0°$ to $40°$ C., followed by the replacement of the protecting group $G_1$ with hydrogen by treating with zinc or zinc combined with copper in the presence of acetic acid at a temperature ranging from $30°$ to $60°$ C. or by treating with an inorganic or organic acid or acetic acid in solution in an aliphatic alcohol containing 1 to 3 carbon atoms or an aliphatic ester in the presence of zinc or zinc combined with copper.

23. The process of claim 15, wherein $G_1$ represents an alkoxyacetyl radical and is replaced with a hydrogen atom by treating in an alkaline medium using ammonia in aqueous-alcoholic medium at a temperature of about $20°$ C. or by treating with zinc halide in methanol at a temperature of about $20°$ C.

24. The process of claim 21, wherein the organic acid is selected from hydrochloric acid and acetic acid.

25. The process of claim 21, wherein the aliphatic ester is selected from ethyl acetate, isopropyl acetate, and n-butyl acetate.

26. The process of claim 22, wherein the organic acid is selected from hydrochloric acid and acetic acid.

27. The process of claim 22, wherein the aliphatic ester is selected from ethyl acetate, isopropyl acetate, and n-butyl acetate.

28. The process of claim 15, wherein when $G_3$ represents a radical $—CH_2—Ph$ and is replaced by a hydrogen atom using hydrogenolysis after replacing the protecting group $G_1$.

* * * * *

UNITED STATES PATENT AND TRADEMARK OFFICE
CERTIFICATE OF CORRECTION

PATENT NO. : 5,580,998
DATED : December 03, 1996
INVENTOR(S) : Herve BOUCHARD et al.

It is certified that error appears in the above-indentified patent and that said Letters Patent is hereby corrected as shown below:

Claim 1, column 20, line 64, "$R_2$-O -CO" should read --$R_2$-O-CO---.

Signed and Sealed this

Eighth Day of July, 1997

Attest:

BRUCE LEHMAN

Attesting Officer

Commissioner of Patents and Trademarks